United States Patent [19]

Wang et al.

[11] Patent Number: 4,493,698
[45] Date of Patent: Jan. 15, 1985

[54] METHOD OF PERFORMING OPTHALMIC SURGERY UTILIZING A LINEAR INTRA-OCULAR SUCTION DEVICE

[75] Inventors: Carl C. T. Wang, Piedmont, Calif.; Steve Charles, Memphis, Tenn.; Joseph T. Buckingham, Moraga, Calif.

[73] Assignee: Cooper Medical Devices, San Leandro, Calif.

[21] Appl. No.: 470,209

[22] Filed: Feb. 28, 1983

Related U.S. Application Data

[62] Division of Ser. No. 203,143, Nov. 3, 1980, Pat. No. 4,395,258.

[51] Int. Cl.$^3$ .............................. A61M 31/00
[52] U.S. Cl. ........................ 604/51; 604/119
[58] Field of Search ............... 604/22, 119, 48–51, 604/65

[56] References Cited

U.S. PATENT DOCUMENTS

| 3,528,410 | 9/1970 | Banko | 128/24 |
|---|---|---|---|
| 3,528,425 | 9/1970 | Banko | 128/305 |
| 3,618,594 | 11/1971 | Banko | 128/24 A |
| 3,659,607 | 5/1972 | Banko | 128/305 |
| 3,736,938 | 6/1973 | Evvard et al. | 128/305 |
| 3,809,093 | 5/1974 | Abraham | 128/305 |
| 3,945,375 | 3/1976 | Banko | 128/6 |
| 4,019,514 | 4/1977 | Banko | 128/230 |
| 4,084,612 | 4/1978 | Baehr | 137/484.2 |
| 4,117,843 | 10/1978 | Banko | 128/230 |
| 4,157,718 | 6/1979 | Baehr | 128/276 |
| 4,167,943 | 9/1979 | Banko | 128/305 |
| 4,167,944 | 9/1979 | Banko | 128/305 |
| 4,168,707 | 9/1979 | Douvas | 604/22 |
| 4,184,510 | 1/1980 | Murry et al. | 604/22 |
| 4,316,465 | 2/1982 | Dotson, Jr. | 604/22 |
| 4,320,761 | 3/1982 | Haddad | 604/22 |
| 4,324,243 | 4/1982 | Helfgott et al. | 604/22 |
| 4,369,785 | 1/1983 | Rehkopf | 604/119 |

Primary Examiner—C. Fred Rosenbaum
Assistant Examiner—J. L. Kruter
Attorney, Agent, or Firm—Limbach, Limbach & Sutton

[57] ABSTRACT

A method is disclosed in which the suctioning of materials from a surgical zone, such as the human eye, is automatically controlled linearly by means of a pressure transducer continuously sensing the vacuum level of a debris receptacle (for collecting suctioned materials from the surgical zone) when material is being suctioned from the zone. The vacuum level in the debris receptacle is linearly varied when the vacuum level in the receptacle is either raised or lowered depending on the suctioning requirements from the surgical zone and whether or not the vacuum level in the receptacle is greater or lower than a previously determined and desirable vacuum level. The vacuum level of the receptacle may, in part, be controlled and varied, by means of a foot pedal operated by the surgeon.

4 Claims, 3 Drawing Figures

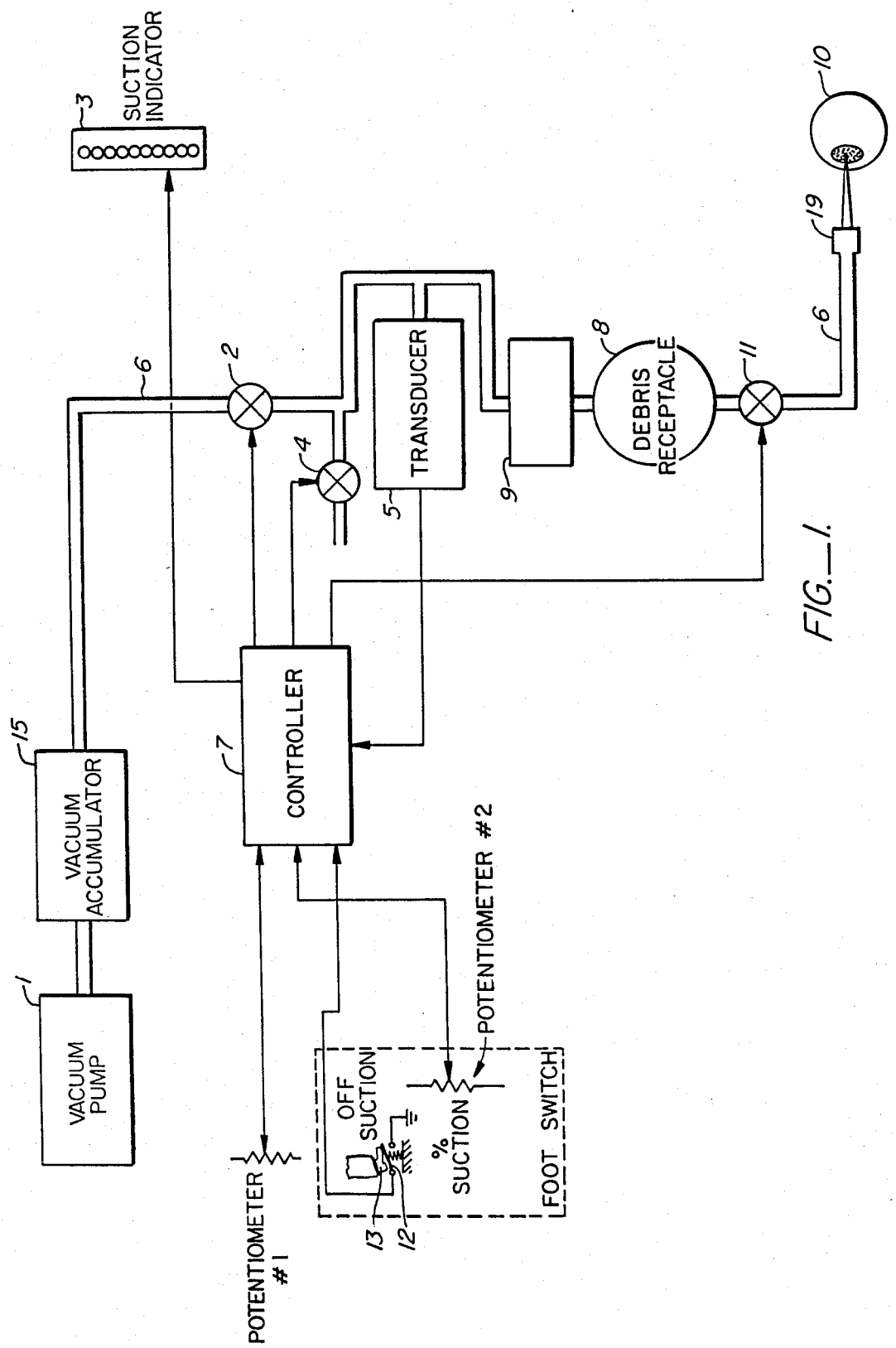
FIG._1.

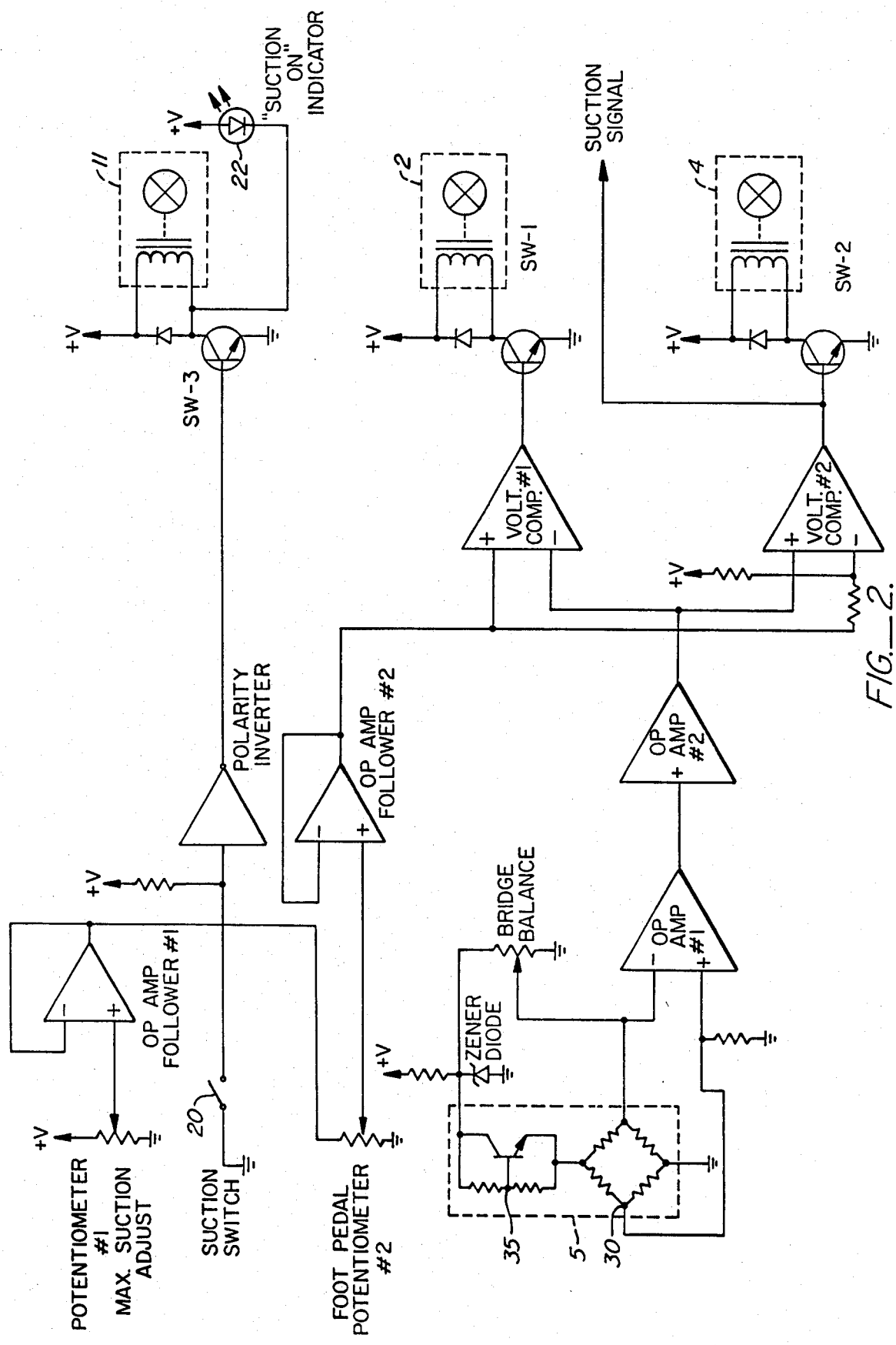
FIG._2.

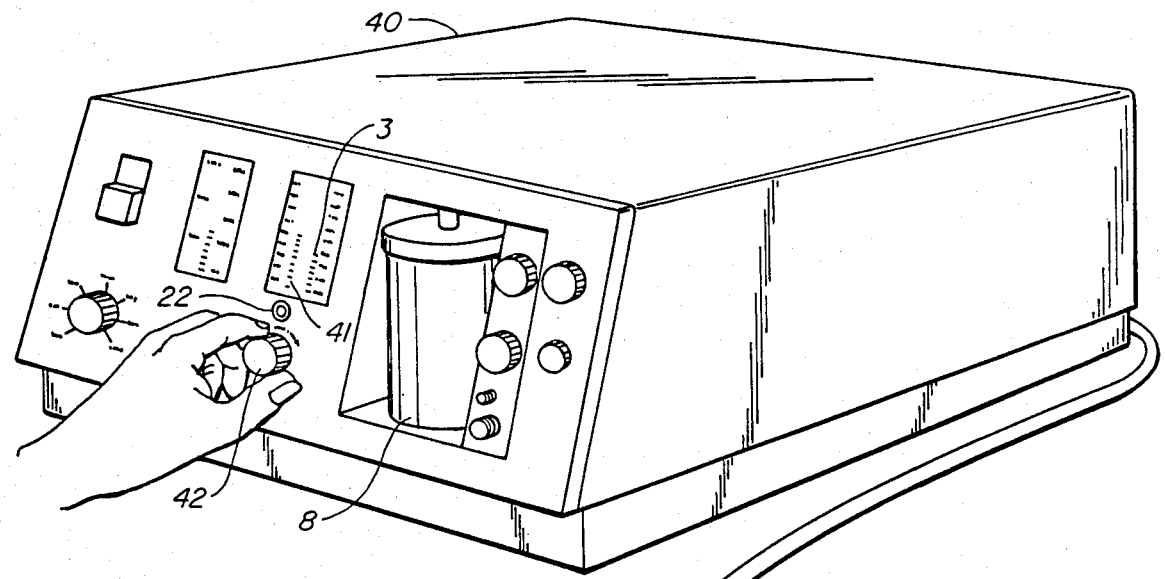
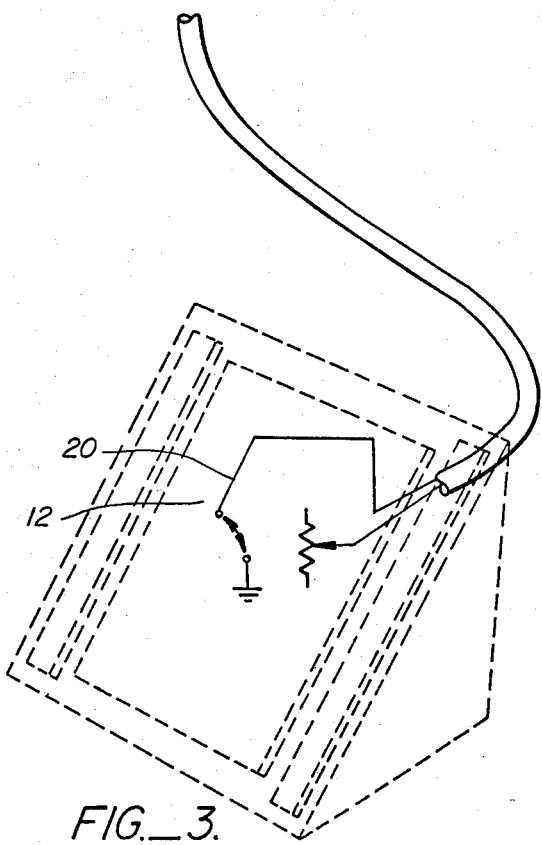
FIG._3.

METHOD OF PERFORMING OPTHALMIC SURGERY UTILIZING A LINEAR INTRA-OCULAR SUCTION DEVICE

This is a division of U.S. application Ser. No. 203,143, filed Nov. 3, 1980, and now issued as U.S. Pat. No. 4,395,258.

FIELD OF THE INVENTION

This invention relates generally to an apparatus for automatically regulating and controlling the vacuum level at which unwanted material is suctioned from a surgical zone, and more particularly the invention relates to an apparatus for use during ophthalmic surgery for automatically regulating and controlling the vacuum level in a debris receptacle for suctioning unwanted material such as vitreous from the interior of the human eye.

BACKGROUND OF THE INVENTION

Various prior art apparatuses have been disclosed which are adapted for holding, cutting and removing tissue from surgical zones, such as the human eye. A number of patents has been issued over the years covering various apparatuses which have sought to automatically (either pneumatically or electrically) control the cutting and suctioning of materials from various surgical zones. In the instances where the surgical zone is the human eye, it is vital that the unwanted material in the eye be severed and removed from the interior sections of the eye without doing damage to the rest of the eye, such as the retina which may result in a detached retina. Damage may result to further interior areas of the eye, such as the choroid which underlies the retina or the optic nerve or the blood vessels associated with the nerve. In order to prevent what may result in a permanent damage to certain portions of the interior eye, it is desirable that during the process, of withdrawing or suctioning unwanted materials from the eye's interior, that any significant residue suction on the interior of the eye when the cutting is at rest be eliminated. Thus, it is most desirable that any vacuum or pressure which must be applied to the eye's interior to withdraw unwanted material from the eye only be applied to the eye's interior when material is actually being suctioned from the area.

Of the numerous prior art apparatuses which are known in the industry, perhaps the O'Malley apparatus which is the subject of U.S. Pat. Nos. 3,815,604 and 3,884,238 is perhaps the most well-known. The apparatus is provided with means for severing the unwanted materials from the main sections of the eye and for applying a vacuum to the eye's interior for withdrawing the vitreous material from the eye. An adjustable bleeder valve is provided in the vacuum line to eliminate residue suctioning on the eye's interior when the cutting action is completed, or is otherwise at rest. This apparatus does not provide, nor is there an appreciation for the need for, linearly controlling the suctioning of material from the eye.

A number of additional patents, including U.S. Pat. Nos. 3,589,363; 3,732,858; 3,805,787; 3,812,855; 3,844,272; 3,920,014; 3,937,222; 3,996,935; and 4,007,742 which have been issued to Anton Banko, have disclosed various apparatuses for both severing and removing unwanted material from various surgical zones, such as vitreous material from the human eye. While each of the foregoing patents has involved some means and apparatus with severing and withdrawing materials from the surgical zone, perhaps the most pertinent of the foregoing patents to the present disclosure is U.S. Pat. No. 3,812,855 which discloses a system for controlling pressurized fluid and suction pressure to and from the surgical zone. While the apparatus does have certain automated features, the pressure of the fluid flowing to and from the operating zone is mechanically sensed. Thus, it follows that the response time for correcting an insufficient or an excess amount of pressurized fluid to or from the surgical zone may well not be uniform and, thus, opens the way for damage to the surgical zone, such as the eye when an insufficient or an excess amount of suctioning pressure is applied to the interior of the eye. The '855 apparatus does, however, provide means, such as bleeder valves, for increasing the amount of pressure to or from the eye in response to an insufficient or an excessive pressure reading, respectively.

A further apparatus is disclosed in U.S. Pat. No. 3,902,495 (Weiss). This apparatus makes use of an ultrasonic hand piece for insertion into the eye, together with a fluidic flow system for use in irrigation and aspiration of a small elastic pressure-responsive chamber, such as the human eye during ultrasonic emulsification of a cataract in the eye. The aspiration portion of the apparatus has a withdrawal hose which has a release valve set to open to atmosphere should the pressure differential in the fluidic withdraw hose exceeds a predetermined pressure.

U.S. Pat. No. 3,693,613 (Kelman) teaches a flow control system to be used in conjunction with a surgical hand piece for the removal of unwanted materials from the surgical zone. The apparatus includes both an irrigation and an aspiration subsystem with the aspirating subsystem comprising a prompt use to remove the unwanted material from the zone and to overcome the friction and other losses throughout the entire fluid system. The aspiration subsystem is further provided with a flow transducer to measuring the rate of flow of fluid from the surgical zone and a vent valve to reduce the flow when necessary to assist in maintaining a relatively constant pressure within the operating zone. An electronic flow control receives signals from the flow transducer and reacts to certain changes in flow signals by sending a signal to the venting valve.

As in all aspirating or suctioning systems, it is important that as the target tissue which must be severed and removed from the surgical zone varies, in mobility, texture and accessibility the suctioning pressure applied to the surgical zone must vary likewise. Thus, it follows that a level of suction which might be suitable for one situation might provoke disaster in another situation particularly when the surgical zone is the human eye. Also, the level of suctioning may not only vary from one human eye to another, but may vary in the same eye depending on the location of the surgery. Consequently, it is highly desirable, technically and therapeutically, that a range of vacuum be selectively and readily available to a surgeon to serve the ever-changing needs which are encountered.

The aforementioned prior art apparatuses have been characterized with a number of problems, such as those which result from manually sensing the pressure along the aspirating conduit such as is the case '855 Banko device. Another problem which is also associated with the manual sensing of the pressure along the aspirating conduit is the obvious delay response time in eliminating the suction force which is applied to the interior of the surgical zone, such as the eye, when the cutting of the vitreous or other unwanted material has ceased. This delay response time may likewise be the result of manually sensing the pressure along the aspirating conduit. Such a delay in responding to the need for more or less suctioning force within the surgical zone can often times result in the damaging disorder known as aphakic-like retina detachment. This retina disorder was also found to be associated with many of the prior art apparatuses which make use of a winding, rotating apparatus for cutting and withdrawing materials from the interior of the human eye.

It was earlier thought that the winding forces of the rotating vitrectomy machines were the only factor in causing retina detachment. But the apparatuses which were disclosed in the O'Malley patent which made use of a reciprocating cutter to eliminate the winding forces, still resulted in a definite incidence of post-operative aphakic-like retina detachment. Thus, the most prevalent problems of the prior art aspirating apparatuses which were the result of an inadequate response time, often times due to manually sensing the pressure along the aspirating conduit, and to the instances of aphakic-like retina detachment which were often times associated with the winding forces of the rotating aspirating apparatuses, remain a part of the prior art aspirating apparatuses for the most part.

BRIEF DESCRIPTION OF THE DRAWING

The advantages and characteristic features of the subject invention will be in part apparent from the accompanied drawings and in part pointed out in the following detail description of the invention in which reference will be made to the accompanied drawings wherein like reference numerals designate corresponding parts, and wherein:

FIG. 1 is a partially schematic view of an apparatus for linearly regulating and controlling the vacuum along a suctioning conduit constructed in accordance with the present invention and incorporating one embodiment of the same;

FIG. 2 is a partially schematic view of a circuit which is employed in the controller of the FIG. 1 apparatus for linearly controlling and regulating the vacuum level in the debris receptacle in response to the vacuum level sensed by the pressure transducer; and FIG. 3 is a perspective view of the exterior of a console incorporating the inventive apparatus of FIG. 1 and the circuit of FIG. 2 together with a foot pedal for operation by the surgeon.

SUMMARY OF THE INVENTION

In view of the still remaining problems of the prior art apparatuses, it follows that there is a need for an apparatus which automatically controls the suctioning of unwanted materials from surgical zones, particularly the human eye, such that there is no active or significant residue suctioning on the interior of the surgical zone, when the cutting action is at rest, and which precludes the human hazard of forgetfulness. There is also a need for such an apparatus which is capable of operating over a wide range of vacuum levels to be selectively and readily available to the surgeon. It is further desirable that the surgeon be able to selectively and readily choose the desired vacuum level without interruption while he continues to perform the surgery.

In our efforts to correct or eliminate the still existing problems with the prior art aspirating apparatuses, we have found that there is a linear relationship between the suction force and the frequency of post-operative aphakic-like retina detachment. We have also found that the incidence of aphakic-like retinal detachment decreases drastically with a decreased pre-set maximum suction force at which the apparatus may be operated. Accordingly, we have invented an apparatus and a method which can automatically regulate and control the suctioning of materials from a surgical zone, such as the human eye, where the suctioning force is linearly controlled to be varied up to a pre-set maximum level and where the periodic suctioning level can be controlled by the surgeon without interrupting the surgery. In accordance with our invention, we have invented an apparatus and method which can automatically regulate and linearly control the vacuum level in a debris receptacle, for withdrawing unwanted materials from the surgical zone, by continuously sensing the vacuum level of the receptacle and by automatically increasing the vacuum level in the receptacle by a percentage amount of the maximum vacuum level at which the apparatus will operate, in response to an insufficient vacuum level being sensed in the receptacle, and by automatically decreasing the vacuum level of the receptacle by a percentage or fraction of the maximum vacuum level, in response to an excessive vacuum level being sensed in the debris receptacle. Our apparatus is desirable and unique in that it (1) linearly controls and adjusts the vacuum level of the debris receptacle and (2) allows for the surgeon to operate the controls by means of a foot pedal or otherwise, during surgery without the necessity of interrupting the surgery or requiring the assistance of another.

DETAILED DESCRIPTION OF THE PREFERRED EMBODIMENTS

The present invention provides a means for linearly controlling the vacuum level in a debris receptacle or conduit which is being used during surgery to withdraw unwanted material from a surgical zone, such as vitreous from the interior of the human eye. As will become evident from the following explanation and the drawings, the present invention is useful in many surgical applications but, for purposes of illustration, the human eye will be used.

In accordance with the invention, FIG. 1 illustrates a schematic view of an apparatus for use in linearly controlling the vacuum level in a debris receptacle 8 and a conduit 6 used for suctioning unwanted materials from the interior of eye 10 along conduit 6 and into receptacle 8. A cannula or probe 19 is inserted into eye 10 for either cutting away unwanted material from the interior of the eye and/or suctioning the unwanted material out of the eye along conduit 6 and into receptacle 8. Receptacle 8 is maintained at a desired vacuum level by means of vacuum pressure being supplied to receptacle 8 from pump 1 and vacuum accumulator 15. Accumulator 15 is used to remove the pulses and vibrations from the vacuum pressure supplied by pump 1. That is, accumulator 15 acts as a smoothing filter for the output from pump 1. A pressure transducer 5 is used to continuously sense the vacuum level along conduit 6 and in debris receptacle 8. A controller 7 is employed to receive an electrical signal from transducer 5 indicating the vacuum level of receptacle 8 and to compare this signal with the desired vacuum level signal which is received from potentiometer #2. In the present embodiment potentiometer #2 is being operated by the surgeon as a foot pedal. Controller 7 operates to either open or close valves 2 and 4 in response to the electrical signal received from transducer 5 indicating the vacuum level of debris receptacle 8.

When in operation, vacuum pump 1 supplies a vacuum pressure to accumulator 15 which filters the undesirable pulses and vibration from the pressure. This vacuum source then selectively supplies a vacuum along conduit 6, through valve 2 (when opened) and to receptacle 8 as transducer 5 indicates an insufficient vacuum level in receptacle 8. Initially, when the apparatus is put into use, potentiometer #1 is pre-set at a maximum vacuum level up to which the surgeon desires to use the apparatus for the given application. Potentiometer #2 is set by the surgeon by turning knob 42 and this value is indicated on the front panel of the operating console 40 (see FIG. 3) at location 41. Probe 19 is inserted into the interior of eye 10 and the surgeon or operator selects the level of vacuum at the location of potentiometer #2 (knob 42) for his immediate needs. Potentiometer #2 is shown to be controlled by a foot pedal 12 which is depressed by the surgeon or operator to select a level of vacuum greater than zero but less than the maximum vacuum level at which potentiometer #1 has been set. Both the maximum vacuum level signal (potentiometer #1) and the vacuum level signal from potentiometer #2 (which is a percentage or fraction of the vacuum level at which potentiometer #1 is set) are passed to controller 7. The vacuum level or the amount of suction chosen by the surgeon for his immediate needs (potentiometer #2) is indicated on the front panel of the operating console at reference numeral 3. This indicator illustrates the amount of vacuum presently being used to suction materials from the interior of eye 10.

Controller 7, after receiving a signal from transducer 5 indicating the level of vacuum along conduit 6 and debris receptacle 8 and by use of the electronics illustrated in FIG. 2 (to be subsequently discussed), compares the signal from transducer 5 with the value of potentiometer #2 to determine if valve 2 or 4 should be opened. Valve 2 is opened by controller 7 if the vacuum level signal from transducer 5 is less than the signal from potentiometer #2. The opening of valve 2 allows additional air to flow from receptacle 8 into the vacuum source (pump 1 and accumulator 15) along conduit 6. Thus, valve 2 is opened in response to an indication that the vacuum level of receptacle 8 is insufficient for adequate suctioning of material from the interior of eye 10. Conversely, where controller 7 senses or determines that the signal from transducer 5 is greater than the signal from potentiometer #2, thus indicating that receptacle 8 is at a vacuum level in excess of that required to safely and adequately suction material from the interior of eye 10, valve 4 is opened to allow atmospheric air to flow into the receptacle 8 and reduce the vacuum. Valve 4 is normally opened (as when no pressure is applied to foot pedal 12 by foot 13) to the atmosphere, thus causing valve 2 to be normally closed.

The surgeon is able to control the level of vacuum in debris receptacle 8 and, thus, control the amount of suctioning along conduit 6 from the interior of eye 10 by varying the distance through which potentiometer #2 is displaced by his foot 13. That is, a slight depression on foot pedal 12 will result in a lesser degree of suctioning from the interior of eye 10 than would a much larger depression or displacement of foot pedal 12. When there is no depression of foot pedal 12, valve 4 is opened and valve 2 is closed and the vacuum level of debris receptacle 8 is not being varied. In addition, valve 11 is closed to prevent flow caused by the higher-than atmospheric pressure in the eye. Once foot pedal 12 is depressed, valve 11 opens and to the extent that transducer 5 senses an insufficient vacuum level in debris receptacle 8, pinch valve 4 closes and pinch valve 2 opens to allow material being suctioned from the interior of eye 10 to flow into receptacle 8. A filter 9 may be inserted between transducer 5 and debris receptacle 8 to prevent the controller system from being ruined by the saline solutions and other debris from receptacle 8 such as pieces of the unwanted materials which are being suctioned from eye 10. Filter 9 shuts off the system between the debris receptacle 8 and the remaining control sections of the system whenever the filter becomes moist.

The FIG. 2 circuit is a simplified schematic diagram which has omitted certain specific details which are well-known to one skilled in the art. The circuit does, however, illustrate a well-known wheatstone bridge 30, having four resistances, which operate as a part of the pressure transducer 5 of FIG. 1. Two of the bridge resistances increase and the other two resistances decrease when the pressure transducer 5 senses an increase (compared to the desired vacuum level) in the vacuum level of receptacle 8. The opposite happens when transducer 5 senses a decrease or an insufficient vacuum level in receptacle 8. A current source 35 is applied to bridge 30 to maintain a precise current to bridge 30. The net resulting change in voltage imbalance in bridge 30 is buffered and amplified by a first operational amplifier (op amp #1) which has its output connected to still a second operational amplifier (op amp #2). The output from op amp #2 is an analog signal representative of the vacuum level in receptacle 8 which has been sensed by transducer 5. This signal is connected to the negative terminal of the first voltage comparator (Volt Comp #1) and to the positive terminal of a second voltage comparator (Volt Comp #2).

The maximum allowable suction level is set with potentiometer #1, resulting in a voltage level which is buffered by op amp follower #1 and applied as the reference voltage, source to potentiometer #2. A fraction of this reference voltage is selected by the foot pedal control, buffered by op amp follower #2 and applied to the positive terminal of voltage comparator #1. A positive offset is added via the two resistors associated with voltage comparator #2. This offset represents the increase in the vacuum level above the desired level in receptacle 8 which must occur before valve 4 is opened. The two voltage comparators also have hysteresis provided through additional resistive networks (not shown) to control the rate of the opening and closing of valves 2 and 4.

Should the first voltage comparator (Volt Comp #1) result in a positive voltage, as would be the case when bridge 30 indicates a decrease or insufficient vacuum valve in receptacle 8, SW-1 is energized by controller 7 to open valve 2. The flow of air out of receptacle 8 along conduit 6 is thus increased, thereby increasing the vacuum level in receptable 8 and thus increase the suctioning of unwanted material from eye 10 along conduit 6 and into receptacle 8. Alternatively, when the second voltage comparator (Volt Comp #2) has a positive voltage output, as is the case when bridge 30 indicates an imbalance representing an increase or an excessive vacuum level in receptacle 8, controller 7 energizes switch SW-2 to open valve 4 to allow atmospheric air to flow into receptacle 8 along conduit 6 to eliminate the excessive vacuum level in receptacle 8.

Valve 2 opens to sustain the vacuum when debris are aspirated from the eye 10. Valve 4 opens to reduce the vacuum in receptacle 8 when a requirement for a reduction in vacuum is indicated via the foot pedal control potentiometer #2. Suction switch 20 is open when the foot pedal 12 is fully released and closed when the foot pedal 12 is depressed to any degree. Closure of the suction switch 20 activates switch 3 (SW-3), which causes pinch valve 11 to open channel 6. When the foot pedal 12 is fully released, pinch valve 11 blocks channel 6. The "suction on" indicator 22 is illuminated when pinch valve 11 opens channel 6.

The above apparatus has the advantage of allowing the surgeon or other operator to linearly control the amount of suctioning from the interior of a surgical zone, such as the human eye, while the surgery operation is being performed. Thus, the surgery and the control of suctioning from the surgical zone may well be performed by a single person. The apparatus is provided with means for continuously sensing the vacuum level in the receptacle and, thus, to maintain a continuous sensing of the degree or amount of suctioning from the surgical zone. Such safe guards clearly result in much more efficient and safe surgery, particularly in surgical zone, such as the human eye where residue suctioning in the interior of the eye may result in permanent eye damage. The apparatus is provided with means to quickly and efficiently correct an excessive or an insufficient vaccum level in the debris receptacle to eliminate any undesirable results or otherwise dangerous situations occurring during surgery. In one of the preferred embodiments of the invention, the surgeon is allowed to control the amount of suctioning which takes place during any period of the surgery by use of a foot pedal. This foot pedal control is suggested simply as a matter of convenience, and is in no way intended to limit the scope of the subject disclosure. Thus, the surgeon or other operator may well control the amount of suctioning being required during any given moment of the surgery by means of some other controls such as a hand-operated device.

Because the above apparatus may be operated using a relatively simple control device, alternate suction controls may be employed within the spirit and scope of the invention by making relatively simple electronic changes. Thus, it is possible to incorporate remote control logic such that the surgeon, or operator may selectively choose between one of three push buttons on a control panel where one button would be to increase suction, another to decrease suction and still another to activate the pinch valve, or the electrical signal may be a feedback signal with the invention being part of feedback controlled system.

It must further be understood that the apparatus constructed in accordance with the invention may incorporate a probe or other cannula device with suitable electronics where the probe may be used to cut materials within the surgical zone as well as suction them. The probe may also be used in a mode where only cutting or suctioning is desired.

While the invention has been shown and described in conjunction with eye surgery, it must be pointed out that the apparatus is useful for regulating and controlling the suctioning of unwanted material from numerous surgical zones where it is important to maintain careful control over the existence and/or amount of suctioning in the surgical zone. As has been previously stated, it must also be understood that numerous alternative circuits can be provided to control the cycling of valves 2, 4 and 11 in order to increase or decrease, respectively, the vacuum level in receptacle 8 and in the case of valve 11 to allow the suctioning of material from the surgical zone into the receptacle chamber.

The invention has been described in detail with particular reference to certain embodiments thereof, but it will be understood that variations and modifications can be effected within the spirit and scope of the invention. The invention is thus limited only by the appended claim.

What is claimed is:

1. A method for performing ophtalmic surgery comprising the following steps:
   adapting a cannula to be inserted into the surgical zone;
   inserting the cannula into the surgical zone;
   maintaining a debris receptacle at a selectable vacuum level for receiving material from the surgical zone, including the steps of
   (1) decreasing the vacuum level of the receptacle through an exhaust valve by automatically and continuously communicating between a transducer, a conduit and a exhaust valve such that the exhaust valve is automatically opened when there is an excessive vacuum level detected in the receptacle,
   (2) increasing the vacuum level of said receptacle by automatically and continuously communicating between the transducer and the conduit to automatically open the conduit between the vacuum supply and the receptacle to increase the vacuum level of the receptacle when an insufficient vacuum level is detected in the receptacle,
   (3) maintaining a first potentiometer at a predetermined level to represent the maximum vacuum level at which said receptacle may be maintained,
   (4) periodically setting a second potentiometer at a value representing a percentage of the value of the first potentiometer where the percentage value is the vacuum level at which the receptacle is maintained for a given application,
   (5) communicating with the vacuum supply and the exhaust valve for comparing the percentage value of the second potentiometer with the detected vacuum level of the pressure transducer to open the conduit and the exhaust valve in response to an insufficient and an excessive level, respectively, in the debris receptacle;
   maintaining a vacuum supply at a predetermined level for varying the vacuum level of the debris receptacle in order that the debris receptacle may be maintained at a selectable vacuum level;
   communicating between a vacuum supply, a debris receptacle, and the cannula with a conduit to selectively increase and decrease the vacuum level of the receptacle when the vacuum of said receptacle is greater or lesser than a predetermined selectable vacuum level; and
   automatically and continuously monitoring the vacuum level of said receptacle with a pressure transducer in order that any variance in the vacuum level of said receptacle may be instantaneously corrected by either increasing or decreasing the vacuum level of said receptacle.

2. The method of claim 1, wherein the step of periodically setting a second potentiometer includes the step of manually controlling and operating said second potentiometer by means of a foot pedal.

3. A method for performing ophalmic surgery comprising the following steps: adapting a cannula to be inserted into a surgical zone;

inserting the cannula into the surgical zone;

maintaining a debris receptacle at a selectable vacuum level for receiving material from the surgical zone, including the steps of (1) decreasing the vacuum level of the receptacle through an exhaust valve by automatically and continuously communicating between a transducer, a conduit, and a exhaust valve, such that the exhaust valve is automatically opened when there is an excessive vacuum level detected in the receptacle, (2) increasing the vacuum level of said receptacle by automatically and continuously communicating between the transducer and the conduit to automatically open the conduit between the vacuum supply and the receptacle to increase the vacuum level of the receptacle when an insufficient vacuum level is detected in the receptacle, (3) providing a normally closed, electrically operable valve on the vacuum line and selectively opening and closing the electrically operable valve to maintain a desired vacuum level in said receptacle, opening said valve to atmosphere when the vacuum level of said debris receptacle exceeds the desired vacuum level to maintain the desired vacuum level in said receptacle and closing said valve to maintain the desired vacuum level in said receptacle, (4) maintaining a first potentiometer at a predetermined value to represent the maximum vacuum level at which said receptacle may be maintained, (5) periodically setting a second potentiometer at a value representing a percentage of the value of the first potentiometer, where the percentage value is the vacuum level at which the receptacle is maintained for any given application, and (6) communicating with the vacuum supply and the exhaust valve for comparing the percentage value of the second potentiometer with the detected vacuum level of the pressure transducer to open the conduit and the exhaust valve in response to an insufficient and an excessive level, respectively, in the debris receptacle;

maintaining a vacuum supply at a predetermined level for varying the vacuum level of the debris receptacle in order that the debris receptacle may be maintained at a selectable vacuum level;

communicating between the vacuum supply, the debris receptacle and the cannula with the conduit to selectively increase and decrease the vacuum level of said receptacle when the vacuum of said receptacle is greater or lesser than a predetermined selectable vacuum level; and automatically and continuously monitoring the vacuum level of said receptacle with a pressure transducer in order that any variance in the vacuum level of said receptacle may be instantaneously corrected by either increasing or decreasing the vacuum of said receptacle.

4. The method of claim 3 wherein the step of periodically setting a second potentiometer includes the step of manually controlling and operating said second potentiometer by means of a foot pedal.

* * * * *